United States Patent [19]

Horowitz et al.

[11] Patent Number: 5,541,294
[45] Date of Patent: Jul. 30, 1996

[54] REMOVAL OF ANTIBODIES FROM BLOOD-DERIVED COMPOSITIONS WHILE RETAINING COAGULATION FACTORS

[75] Inventors: Bernard Horowitz, New Rochelle; Sing N. Chin, New York, both of N.Y.

[73] Assignee: New York Blood Center, Inc., New York, N.Y.

[21] Appl. No.: 419,836

[22] Filed: Apr. 11, 1995

Related U.S. Application Data

[63] Continuation of Ser. No. 890,528, May 28, 1992, abandoned.

[51] Int. Cl.$^6$ .............................. C07K 1/00; B01D 61/00
[52] U.S. Cl. .................... 530/380; 530/381; 530/382; 530/383; 530/384; 530/412; 530/413; 530/417; 525/54.1; 210/198.2; 210/645; 210/651; 210/656
[58] Field of Search ...................... 530/380, 381, 530/382, 383, 384, 412, 413, 417; 525/54.1; 210/198.2, 645, 651, 656; 435/236, 238, 239

[56] References Cited

U.S. PATENT DOCUMENTS

| | | | |
|---|---|---|---|
| 4,137,401 | 1/1979 | Lemieux et al. | 536/116 |
| 4,195,174 | 3/1980 | Lemieux et al. | 536/18 |
| 4,238,473 | 12/1980 | Lemieux et al. | 424/101 |
| 4,308,376 | 12/1981 | Lemieux et al. | 536/18 |
| 4,362,720 | 12/1982 | Lemieux et al. | 424/180 |
| 4,664,913 | 5/1987 | Mielke et al. | 424/101 |
| 4,764,369 | 8/1988 | Neurath et al. | 424/89 |
| 5,094,960 | 3/1992 | Bonomo | 436/178 |
| 5,149,425 | 9/1992 | Mazid | 210/198.2 |

FOREIGN PATENT DOCUMENTS

| | | |
|---|---|---|
| 0141939A2 | 8/1984 | European Pat. Off. . |
| 0276342 | 1/1987 | European Pat. Off. . |
| 0276342 | 8/1988 | European Pat. Off. . |
| 1544908 | of 0000 | United Kingdom . |
| 1544908 | 4/1979 | United Kingdom . |
| WO86/05397 | 3/1985 | WIPO . |
| WO8605397 | 9/1986 | WIPO . |

OTHER PUBLICATIONS

"Virus–Free Protein Containing Composition Preparation Obtained By Treatment With Trialkylphosphates Followed By Affinity Chromatography", Derwent Publications Ltd., Jul. 13, 1990.

"Virus Free Protein Containing Composition Preparation" by Derwent.

Theodorsson et al, *Blood*, vol. 61, No. 5, pp. 973–981, May 1983.

Lieburou et al, *Proc. Natl. Acad. Sci. USA*, vol. 82, pp. 3879–3883, Jun. 1985.

Tharakau et al, *Journal of Chromatography*, vol. 595, pp. 103–111, 1992.

*Primary Examiner*—Elizabeth C. Weimar
*Assistant Examiner*—Abdel A. Mohamed
*Attorney, Agent, or Firm*—Amster, Rothstein & Ebenstein

[57] ABSTRACT

This invention relates to methods of removing undesired antibodies from blood-derived compositions containing both the antibodies and coagulation factors, such that the coagulation factors are substantially retained in the composition. The undesired antibodies may be blood group antibodies. This invention also relates to compositions in which undesired antibodies have been removed and desired coagulation factors are retained. This invention further relates to methods of inactivating virus and removing undesired antibodies from blood-derived compositions containing virus, antibodies and coagulation factors without removing coagulation factors therefrom, and to the resulting compositions.

9 Claims, No Drawings

REMOVAL OF ANTIBODIES FROM BLOOD-DERIVED COMPOSITIONS WHILE RETAINING COAGULATION FACTORS

This is a continuation of application Ser. No. 07/890,528, filed on May 28, 1992, now abandoned.

FIELD OF THE INVENTION

This invention relates to the removal of undesired antibodies from blood-derived compositions, which compositions contain both undesired antibodies and desired coagulation factors. The removal of the antibodies is effected in such a manner that the desired coagulation factors are substantially retained in the resulting compositions. More particularly, the invention is directed to contacting a blood-derived composition containing blood group antibodies and coagulation factors with a resin which includes antigens specific for the blood group antibodies to be removed from the composition, the resin being selected such that its use does not also result in the removal of the desired coagulation factors from the composition.

BACKGROUND OF THE INVENTION

As used herein, the term "blood-derived compositions" includes whole blood, blood plasma, blood plasma fractions, blood plasma precipitate (e.g., cryoprecipitate, ethanol precipitate or polyethylene glycol precipitate), supernatant (e.g., cryosupernatant, ethanol supernatant or polyethylene glycol supernatant) or other compositions derived from human or animal blood and characterized by the presence of coagulation factors and blood group or other undesired antibodies. Blood-derived compositions also include purified coagulation factor concentrates (e.g., Factor VIII concentrate, Factor IX concentrate, Fibrinogen concentrate) prepared by any of various methods including ion exchange, affinity, gel permeation, and/or hydrophobic chromatography or by differential precipitation.

The term "blood group" is used to identify any one of the many types into which a person's blood may be classified, based on the presence or absence of certain inherited antigens on the surface of the red blood cells. Blood of one group contains or may contain antibodies in the serum that react against the cells of other groups. These antibodies are referred to herein as "blood group antibodies" and are also referred to in the art as isoagglutinins.

There are more than thirty blood group systems, one of the most important of which is the ABO system. This system is based on the presence or absence of antigens A and B. Blood of groups A and B contain antigens A and B, respectively. Group AB contains both antigens, and group O contains neither.

The major blood group antibodies are anti-A and anti-B antibodies, which are mainly of the IgM and IgG isotypes. Blood of group A contains antibodies to antigen B. Blood of group B contains antibodies to antigen A. Blood of group AB has neither antibody, and blood of group O has both. A person whose blood contains either (or both) of the anti-A and anti-B antibodies cannot receive a transfusion of blood containing the corresponding antigens.

Specifically, when blood group antibodies are mixed with blood of an incompatible group, the antibodies coat the red blood cells of the incompatible group and cause the agglutination (clumping or sticking together) thereof. Incompatible blood group antibodies can fix complement, cause transfusion reactions and induce hemolysis, which is the destruction of red blood cells. Hemolysis can lead to anemia and other complications.

In order to avoid immunohemolysis and transfusion reactions caused by blood group antibodies in donor plasma which are incompatible with the blood group type of the blood transfusion recipient, the donor plasma and the blood group type of the recipient must be cross-matched or typed and screened.

In an effort to avoid the necessity of cross-matching and create "universal" blood-derived compositions (compositions that can be administered without regard for the blood group of donor and recipient), methods have been developed for removing blood group antibodies from blood-derived compositions. Typically, artificial antigens specific for the blood group antibody which is to be removed are attached to a support, such as a resin, which is then used to remove such antibodies. Examples of such artificial antigens can be found in U.S. Pat. Nos. 4,362,720, 4,308,376, 4,238,473, 4,195,174 and 4,137,401, all of which have been assigned to Chembiomed, Ltd. of Edmonton, Canada.

As such, commercially available resins, such as Synsorb and Chromosorb, when used with appropriate antigens, are able to remove blood group antibodies from blood-derived compositions. However, because Synsorb, Chromosorb and many other commercially available resins non-specifically adsorb coagulation factors, removal of blood group antibodies from blood-derived compositions with such resins also results in the undesired removal of an unacceptably high level of coagulation factors from such compositions.

Coagulation factors, also known as blood clotting factors, are substances present in blood that undergo a series of chemical reactions which lead to the conversion of the blood from a liquid to a solid state. Coagulation factors include Factor V, Factor VIII, Factor IX and Factor XI. Since these factors work sequentially (in a series of reactions termed a "cascade"), lack of a sufficiently high level of any one of these factors in the blood results in the inability of the blood to clot. Hence, the removal of any coagulation factors from blood-derived compositions for use in humans or animals to replace low or missing coagulation factors is not desired and is dangerous. As a result, a need has arisen to develop a method of removing blood group antibodies from blood-derived compositions so that said compositions may be "universal", without removing coagulation factors from said compositions so that blood clotting ability is not impaired.

Another problem with the resins (i.e., Synsorb and Chromosorb) currently used to remove blood group antibodies from blood-derived compositions is that such resins are only capable of completely removing blood group antibodies from such compositions at a volume ratio of 30 ml of composition per 1 ml of resin. This required ratio results in the inefficient removal of blood group antibodies. Hence, a need has also arisen to develop a more efficient method of removing blood group antibodies from blood-derived compositions without removing coagulation factors therefrom.

A still further problem connected with the removal of blood group antibodies from blood-derived compositions is that such compositions may be virus-containing. As such, any blood group antibody removal technique must also include or be compatible with virus-inactivation methods.

It is therefore an object of this invention to provide methods for removing blood group antibodies from blood-derived compositions, such that said compositions may be universal, without substantially removing coagulation factors from the compositions.

It is another object of this invention to provide methods for making blood-derived compositions from compositions which initially contained undesired antibodies and coagulation factors therein, but after treatment of such compositions with the methods of this invention, are effectively free of the undesired antibodies and have substantially retained their coagulation factors.

It is still another object of this invention to provide blood-derived compositions which, having once contained both blood group antibodies and coagulation factors, are effectively blood group antibody-free but have substantially retained their coagulation factors.

It is a further object of this invention to provide methods for making blood-derived compositions from compositions which initially contained active virus, undesired antibodies and coagulation factors therein, but after treatment of such compositions with the methods of this invention, are virus-inactivated and effectively free of the undesired antibodies, but have substantially retained their coagulation factors.

It is a still further object of this invention to provide virus-inactivated blood-derived compositions which, having once contained active virus, blood group antibodies and coagulation factors, are virus-inactivated and effectively blood group antibody-free, but have substantially retained their coagulation factors.

It is an additional object of this invention to provide a resin-antigen combination capable of removing specific undesired antibodies from blood-derived compositions while permitting the substantial retention of desired coagulation factors.

It is yet another object of this invention to provide a resin-antigen combination capable of removing blood group antibodies from blood-derived compositions while permitting the substantial retention of desired coagulation factors.

SUMMARY OF THE INVENTION

This invention is directed to methods for removing blood group antibodies from blood-derived compositions to render said compositions universal with respect to blood group without substantially removing coagulation factors from said blood-derived compositions so as to avoid risks inherent in administering compositions with diminished levels of blood clotting factors. The methods of the invention include contacting blood-derived compositions which contain blood group antibodies and one or more coagulation factors with a resin which includes antigens capable of binding (and therefore removing) the blood group antibodies. The resin is selected such that its use does not result in removal of the coagulation factors from the composition. This invention is further directed to blood-derived compositions which, having once contained both blood group or other undesired antibodies and coagulation factors, are effectively antibody-free but have substantially retained their coagulation factors. In addition, this invention is directed to virus-inactivated blood-derived compositions which, having once contained active virus, blood group antibodies and coagulation factors are virus-inactivated and effectively blood group antibody-free, but have substantially retained their coagulation factors. This invention is also directed to methods for making said virus-inactivated blood-derived compositions.

DETAILED DESCRIPTION OF THE INVENTION

This invention relates to methods for removing blood group antibodies from blood-derived compositions containing both blood group antibodies and coagulation factors wherein said resulting blood group antibody-free blood-derived compositions retain a high percentage of their coagulation factors. This invention is also directed to blood group antibody-free compositions containing coagulation factors. In the methods of this invention, a blood-derived composition which contains both blood group antibodies and coagulation factors is put into contact (e.g., by chromatography or by batch adsorption) with a resin capable of removing blood group antibodies without removing coagulation factors therefrom. Such resin is covalently bonded to blood group or type-specific (e.g., type-A, type-B or type-D) antigens, such as synthetic oligosaccharide antigens or protein antigens. The blood group or type-specific antigens on the resins bind to the blood group antibodies in the blood-derived composition, while allowing the remainder of the blood-derived composition to pass through the resin intact.

The resin-antigen combinations used in the methods of this invention are capable of removing blood group antibodies from blood-derived compositions without substantially removing coagulation factors therefrom. The inventors have discovered that the retention of coagulation factors is apparently effected by the resin selected and more particularly the matrix of the resin. Examples of commercially available resins and the corresponding matrix for each are shown in Table I below.

TABLE I

| Resin | Resin Matrix |
| --- | --- |
| Synsorb | crystalline silica |
| Antab | agarose |
| Synsorb B-PS | crystalline silica coated by the manufacturer to reduce ionic adsorption |
| Chromosorb G | crystalline silica with greater ligand spacing |
| Toyopearl | alkylmethacrylate polymer |
| Prep C18 | microparticulate porous glass |

Commercially available resins currently used in the removal of blood group antibodies are unable to remove blood group antibodies from blood-derived compositions without also removing an unacceptably high level of coagulation factors therefrom. However, the inventors have discovered that the commercially available Toyopearl (Toyo-Haas, Japan) resin, which has a polymethacrylic matrix (also called backbone), may be used with an appropriate antigen to remove blood group antibodies while surprisingly retaining over 90% of the coagulation factors. Further, the Toyopearl resin-antigen combination may be used to more efficiently remove blood group antibodies from plasma at a high volume of 120 ml plasma per 1 ml of resin.

Another resin which the inventors have discovered may be used to remove blood group antibodies without removing a high level of coagulation factors is the resin Prep C18 ("C18") (Waters Division of Millipore, Inc.). C18 resin has a matrix of microparticulate porous glass, and is hydrophobic. If hydrophobicity is not required, microparticulate porous glass alone may be used as the resin.

Immunoaffinity techniques, such as chromatography and batch adsorption, may be used to remove blood group antibodies from blood-derived compositions without substantially removing coagulation factors therefrom. Where chromatography is used, a resin-antigen combination capable of removing blood group antibodies without substantially removing coagulation factors is equilibrated in a buffer, such as PBS or saline, with a pH in the range of about 5.5–9.5. The preferred pH range is 6.4–7.8. The equilibration temperature is about 0°–45° C., with the preferred temperature being room temperature. A blood-derived composition containing blood group antibodies and coagulation factors is then run through the resin column with a contact time in the range of about 1–60 minutes, with 4–10 minutes being the preferred contact time.

Another immunoaffinity procedure which may be used to remove blood group antibodies from blood-derived compositions without substantially removing coagulation factors therefrom is batch adsorption. To utilize batch adsorption, a resin capable of removing blood group antibodies from blood-derived compositions without substantially removing coagulation factors therefrom is added to a composition containing blood group antibodies and coagulation factors in a suitable container (e.g., a polypropylene bottle or a stainless steel tank), mixed at a temperature of 0° to 45° C., with the preferred temperature being ambient, for a period of at least 1 hour, with a preferred period being 4 hours, the resin sedimented by normal gravity or centrifugation and then the unbound composition is removed.

Blood-derived compositions which may be used include blood products, blood plasma, blood plasma precipitate (e.g., cryoprecipitate, ethanol precipitate or polyethylene glycol precipitate), supernatant (e.g., cryosupernatant, ethanol supernatant or polyethylene glycol supernatant) or any other composition derived from blood and characterized by the presence of one or more coagulation factors and blood group antibodies.

In order to determine whether blood group antibodies have been removed from a blood-derived composition, it is necessary to determine the blood group antibody titer within the composition after contacting the composition with a resin-antigen combination of the invention. This may be performed by direct blood group antibody test (DAT) or indirect Coombs test (ICT). In order to determine the amount of recovery of coagulation factors in the blood-derived compositions treated by the methods of this invention, the treated blood-derived compositions may be assayed for activities of the coagulation factor or factors of interest, e.g., Factors V, VIII, IX and XI, by determining the degree of correction in the clotting time of a plasma deficient in the particular factor or factors in the presence of activated partial thromboplastin (APTT) reagent, or by other assay methods known in the art. In order to evaluate the protein content and distribution of the blood-derived compositions treated by the methods of this invention, protein content may be measured by Biuret reagent and protein distribution may be measured by SDS-polyacrylamide gel electrophoresis.

Virus-containing blood-derived compositions may also be treated by the methods of this invention. Either before or after removing blood group antibodies from a virus-containing composition utilizing the methods of this invention, said viruses are inactivated. The virus-inactivation methods discussed in U.S. Pat. No. 4,764,369 issued to Neurauth et al., dated Aug. 16, 1988, entitled "Undenatured Virus-Free Biologically Active Protein Derivatives," which is incorporated herein by reference, may be used. The removal of process chemicals used in virus-inactivation methods is discussed in U.S. Pat. No. 5,094,960, issued to Richard J. Bonomo on Mar. 10, 1992, entitled "Removal of Process Chemicals From Labile Biological Mixtures By Hydrophobic Interaction Chromatography," which is incorporated herein by reference.

Compositions which are to be virus-inactivated may be treated with an effective amount of di- or trialkylphosphate reagents, such as 1% tri(n-butyl)phosphate (TNBP) and 1% Triton X-100 at 30° C. for four hours. The added reagents are then removed by extracting said agents with soy bean oil rand chromatography on insolubilized C18 resin. These methods allow for virus-inactivation of such blood-derived compositions, without denaturing the proteins in said blood-derived compositions. Alternatively, other viral inactivation methods may be used, e.g., photodynamic inactivation of viruses in the presence of methylene blue or the thermal inactivation of viruses in the presence of sugars and/or amino acids. Blood group antibody removal may be performed either prior to virus inactivation, following virus inactivation but prior to removal of viral inactivants or protein stabilizers used as part of virus inactivation or following virus inactivation and removal of such viral inactivants and protein stabilizers. The viruses that are inactivated by these methods include vesicular stomatitis virus (VSV), sindbis virus, human immunodeficiency virus (HIV), hepatitis B virus and hepatitis C virus.

EXAMPLES

Example 1: Removal of Anti-A and Anti-B Blood Group Antibodies From Plasma Using Chromatography Resins containing blood group A antigens and blood group B antigens were used to remove blood group antibodies from plasma. Resins containing blood group A antigens are identified by the suffix "A" and included Synsorb A (Chembiomed Ltd., Edmonton, Canada) and Antab A (Monocarb Ltd., Lund, Sweden). Resins containing blood group B antigens are identified by the suffix "B" and included Synsorb B, Synsorb B-PS, Chromosorb G (Chembiomed Ltd., Edmonton, Canada), Toyopearl (Toyo-Haas, Japan) to which blood group antigen B was added by Chembiomed Ltd. at the instruction of the inventors, and Antab B (Monocarb Ltd., Lund, Sweden). All of the resins were evaluated for removal of anti-A and anti-B blood group antibodies from whole human blood plasma.

The resins were first equilibrated in phosphate buffered saline, pH 7.2 and placed in 1×5 cm polypropylene chromatographic columns. Human plasma was then pumped through the resins at a linear flow rate of 19 cm/hr, collecting 2 ml fractions. The initial plasma and the unbound column eluate were assayed for IgM antibody by direct blood group antibody test (DAT) and for IgG antibody by the indirect Coombs test (ICT). The results are shown in Table II below. The results are expressed as the volume of plasma from which both IgG and IgM antibody directed against A or B antigen were eliminated, as determined by the DAT and ICT test methods. As shown in Table II, all of the resins successfully removed blood group antibodies, although certain resins had substantially higher capacities than other resins for such removal. Antab A, Antab B and Toyopearl with B added had the highest capacities for removing blood group antibodies from plasma. The capacity for blood group antibody removal is shown as the volume (ml) of plasma per volume (ml) of resin at which blood group antibodies were totally eliminated from the plasma.

TABLE II

| Resin | Column Capacity for Anti-A or -B Antibody (ml plasma/ml resin) |
|---|---|
| Synsorb A | 14 |
| Antab A | 187 |
| Synsorb B | 30 |
| Synsorb B-PS | 10 |
| Chromosorb G | 10 |
| Toyopearl with B added | 120 |
| Antab B | 312 |

Example 2: Retention of Coagulation Factors In Plasma Using Various Resins and Chromatography The resins described in Example 1 and three additional resins, C18 (Waters Division of Millipore, Inc.), CPI and Spherosil (IBF Biotecnics, France) were used in chromatography columns and assessed for their binding of coagulation factors in the plasma. All of the resins were equilibrated and the chromatography was performed as described in Example 1. Input plasma and eluted unbound plasma were assayed for the activities of Factors V, VIII, IX and XI by determining the degree of correction in the clotting time of plasma deficient in each of those particular coagulation factors in the presence of activated partial thromboplastin (APTT) reagent. For Factor V, the reagent was thromboplastin, instead of APTT reagent. The results are shown in Table III below. Of all the resins evaluated, only Toyopearl and C18 provided a recovery greater than 85% of each of the measured coagulation factors.

Example 3: Retention of Coagulation Factors In Plasma Using Synsorb, Chromosorb and Toyopearl Resins, and Chromatography Synsorb, Chromosorb and Toyopearl resins were each equilibrated in PBS, pH 7.4 at room temperature. Plasma was loaded onto each resin at a ratio of 30 ml plasma/1 ml resin for the Synsorb and Chromosorb resins, and a ratio of 120 ml plasma/1 ml resin for the Toyopearl resin, with a contact time of 4 minutes for each of the resins. The results are shown in Table IV below. The percentage of coagulation factor recovery of Factors V, VIII, IX and XI for Toyopearl greatly exceeded the percentage of coagulation factor recovery for Synsorb and Chromosorb. "n" represents the number of experiments performed for each of the resins. The Coagulation factor recovery percentage is an average of each of the column runs for each resin. For all of the column runs, the blood group antibody titer was reduced from $2^4$ to $2^0$ (i.e., an undetectable level) after running the plasma through the columns.

TABLE IV

| A | B | C | D | E | F | G | H | I |
|---|---|---|---|---|---|---|---|---|
| RESIN | % REC FV | % REC FVIII | % REC FIX | % REC FXI | AVE. COAG. FCTRS | n | CAPACITY* ML.P./ML.RES | |
| SYNSORB | 80% | 71% | 82% | 36% | 67% | 4 | 30 | |
| CHROMOSORB | 79% | 76% | 88% | 72% | 79% | 5 | 30 | |
| TOYOPEARL | 91% | 91% | 94% | 87% | 91% | 2 | 120 | |

* = MAXIMAL VOLUME PLASMA/ML RESIN IN WHICH THE ANTIBODY IS TOTALLY ADSORBED

Example 4: Removal of Blood Group Antibodies and Retention of Coagulation Factors in Plasma Using Toyopearl Resin and Chromatography Toyopearl resin with B antigen added was equilibrated in PBS, pH 7.4 at room temperature. Both virus-containing plasma and virus inactivated plasma were loaded onto the equilibrated Toyopearl resin at a ratio of 120 ml plasma/1 ml resin with a contact time of 4 minutes. Prior thereto, the virus-containing plasma was treated with 1% tri(n-butyl)phosphate and 1% Triton X-100 at 30° C. for 4 hours to inactivate virus. The virus-inactivated plasma was then clarified by filtration through a 1 micron glass fiber filter.

The results of blood group antibody removal and coagulation factor retention of the virus-containing plasma and the

TABLE III

| | Percent Recovery | | | | |
|---|---|---|---|---|---|
| Resin | Factor V | Factor VIII | Factor IX | Factor XI | Average of All Factors |
| Synsorb A | 71% | 75% | 95% | 32% | 68% |
| Antab A | na | na | na | na | na |
| Synsorb B | 80% | 71% | 82% | 36% | 67% |
| Synsorb B-PS | 63% | 67% | 71% | 50% | 63% |
| Chromosorb G | 55% | 58% | 63% | 60% | 59% |
| Toyopearl with B added | 91% | 91% | 94% | 87% | 91% |
| Antab B | na[4] | na | na | na | na |
| Prep C18[1] | 95% | 94% | 99% | 92% | 95% |
| CPI[2] | 25% | 55% | 63% | 60% | 51% |
| Spherosil[2] | 11% | 25% | act[3] | act[3] | 18%[5] |

[1] = Waters Division of Millipore, Inc.
[2] = IBF Biotecnics, France
[3] = act: recovery exceeded 300% of initial, indicative of proteolytic activation.
[4] = na: product no longer available
[5] = average of two factors virus-inactivated plasma run through Toyopearl resin are shown in Table V below. The virus-inactivated plasma is denoted SD-plasma. The percentage of coagulation factor recovery for the SD-plasma run through Toyopearl resin was between 82.40% and 91.70% for Factors V, VIII, IX and XI with the average recovery of all factors being 88.53%. The percentage of coagulation factor recovery for the virus-containing plasma run through Toyopearl resin was between 91.40 and 96.80% for Factors V, VIII, IX and XI with the average recovery of all factors being 93%. Coagulation factor recovery was determined when blood group antibodies were completely removed from the plasma.

TABLE V

| A | B | C | D | E | F | G | | H | |
|---|---|---|---|---|---|---|---|---|---|
| SAMPLE | FV | FVIII | FIX | FXI | AVG | DAT* | | ICT** | |
| | % REC. | % REC. | % REC. | % REC. | % REC. | ST. | END | ST. | END |
| Plasma | 92.20% | 91.60% | 96.80% | 91.40% | 93% | 2E4 | 2EO | 2E4 | 2E1 |
| SD-Plasma | 89.10% | 90.90% | 91.70% | 82.40% | 88.53% | 2E4 | 2EO | 2E4 | 2E1 |

* = DIRECT ANTIGLOBULIN TEST
** = INDIRECT COOMBS TEST

Example 5: Removal of Blood Group Antibodies and Retention of Coagulation Factors in Virus-Inactivated Plasma Using Toyopearl Resin and Chromatorgraphy Plasma from blood group A donors was treated with 1% tri(n-butyl)phosphate and 1% Triton X-100 at 30° C. for 4 hours to inactivate virus. The virus-inactivated plasma was then clarified by filtration through a 1 micron glass fiber filter. Next, the clarified plasma was passed through a column of Toyopearl combined with B antigen at a ratio of 10 ml resin/1 liter of plasma with a contact time of 4 minutes. The titer of anti-B blood group antibodies was $2^4$ prior to running the plasma through the Toyopearl column. After running the plasma through the column, no anti-B antibody was detected in the eluate plasma, as measured by DAT and ICT. Coagulation factor recovery was greater than 90% for each factor. In addition, the total amount of protein and the distribution of protein remained unchanged as measured by Biuret reagent and by SDS-polyacrylamide gel electrophoresis, respectively.

Example 6: Removal of Anti-B Blood Group Antibodies and Retention of Coagulation Factors in Plasma Using Toyopearl Resin and Batch Adsorption Two ml of Toyopearl combined with B antigen was added to 120 ml of human blood plasma in a polypropylene bottle. The mixture was stirred by rocking at ambient temperature for 4 hours. The resin was settled by centrifugation and the unbound supernatant plasma was removed. The titer of anti-B blood group antibody was measured by both DAT and ICT, as in Example 1. The anti-B blood group antibody was reduced from a starting titer of $2^4$ to an undetectable titer $2^0$. Greater than 90% of each coagulation factor was retained in the plasma.

Although the invention herein has been described with reference to particular embodiments, it is to be understood that these embodiments are merely illustrative of various aspects of the invention. For example, the method of the present invention could be used to remove any undesired antibody while not substantially removing coagulation factors. Thus, it is to be understood that numerous modifications may be made in the illustrative embodiments, and other arrangements may be devise without departing from the spirit and scope of the invention.

We claim:
1. A method for removing a selected antibody from a blood-derived composition which contains said antibody and Factor V, Factor VIII, Factor IX and Factor XI coagulation factors while retaining on average at least 85% of said coagulation factors, said method comprising contacting said composition with a resin-antigen combination to remove substantially all of said antibody, wherein said resin comprises an alkylmethacrylate polymer or a microparticulate porous glass and said antigen is specific for said antibody.

2. The method of claim 1 wherein said blood-derived composition is selected from the group consisting of blood products, blood plasma and other compositions derived from blood and characterized by the presence of said coagulation factors and said antibody.

3. The method of claim 1 wherein the contacting is effected by chromatography.

4. The method of claim wherein the contacting is effected by batch absorption.

5. The method of claim 1 wherein said resin is an alkylmethacrylate polymer.

6. The method of claim 1 wherein said resin is a microparticulate porous glass.

7. The method of claim 1 wherein said method results in a retention of at least 85% of each of said coagulation factors.

8. The method of claim 1 wherein said antibody is a blood group antibody.

9. The method of claim 8 wherein said antibody comprises an anti-A, an anti-B, or both an anti-A and an anti-B blood group antibody.

* * * * *